(12) United States Patent
Siccardi et al.

(10) Patent No.: US 11,602,355 B2
(45) Date of Patent: Mar. 14, 2023

(54) CUTTING GUIDE FOR PERIACETABULAR OSTEOTOMY AND KIT FOR PERIACETABULAR OSTEOTOMY

(71) Applicant: MEDACTA INTERNATIONAL SA, Castel San Pietro (CH)

(72) Inventors: Francesco Siccardi, Castel San Pietro (CH); Sascha Berberich, Castel San Pietro (CH); Matteo Ponzoni, Castel San Pietro (CH); Matteo Ferrari, Castel San Pietro (CH)

(73) Assignee: Medacta International SA, Castel San Pietro (CH)

( * ) Notice: Subject to any disclaimer, the term of this patent is extended or adjusted under 35 U.S.C. 154(b) by 217 days.

(21) Appl. No.: 16/956,250

(22) PCT Filed: Dec. 17, 2018

(86) PCT No.: PCT/IB2018/060160
§ 371 (c)(1),
(2) Date: Jun. 19, 2020

(87) PCT Pub. No.: WO2019/123192
PCT Pub. Date: Jun. 27, 2019

(65) Prior Publication Data
US 2021/0077119 A1   Mar. 18, 2021

(30) Foreign Application Priority Data
Dec. 22, 2017 (IT) .......... 102017000148714

(51) Int. Cl.
*A61B 17/15* (2006.01)
*A61B 17/17* (2006.01)

(52) U.S. Cl.
CPC ........ *A61B 17/151* (2013.01); *A61B 17/1746* (2013.01)

(58) Field of Classification Search
CPC ... A61B 17/151; A61B 17/15; A61B 17/1746; A61B 17/8066; A61B 17/7055
See application file for complete search history.

(56) References Cited

U.S. PATENT DOCUMENTS

| 5,112,337 A | 5/1992 | Palous et al. |
| 5,928,232 A | 7/1999 | Howland et al. |

(Continued)

FOREIGN PATENT DOCUMENTS

| CN | 206560458 U | 10/2017 |
| DE | 4219939 | 12/1993 |

(Continued)

OTHER PUBLICATIONS

Machine English translation of Hanada et al. JP-6324194. (Year: 2022).*

(Continued)

*Primary Examiner* — Amy R Sipp
(74) *Attorney, Agent, or Firm* — Meunier Carlin & Curfman LLC

(57) ABSTRACT

A cutting guide for periacetabular osteotomy comprises at least a first main body having a longitudinal opening for the insertion of a cutting instrument, extending from a first end to a second end of the first main body and at least two positioning and fixing arms extending away from the first main body from opposite sides with respect to the longitudinal opening, in order to correctly position the first main body on a bone and fix it thereto through respective fastening members.

14 Claims, 9 Drawing Sheets

(56) References Cited

U.S. PATENT DOCUMENTS

| | | | |
|---|---|---|---|
| 6,007,537 A * | 12/1999 | Burkinshaw | A61B 17/155 606/88 |
| 8,758,357 B2 | 6/2014 | Frey | |
| 8,870,889 B2 | 10/2014 | Frey | |
| 9,198,678 B2 | 12/2015 | Frey et al. | |
| 9,642,633 B2 | 5/2017 | Frey et al. | |
| 9,987,024 B2 | 6/2018 | Frey et al. | |
| 2002/0123668 A1 | 9/2002 | Ritland | |
| 2007/0066977 A1 | 3/2007 | Assell et al. | |
| 2008/0114370 A1 | 5/2008 | Schoenfeld | |
| 2011/0319745 A1 | 12/2011 | Frey | |
| 2012/0053590 A1 * | 3/2012 | Allen | A61F 2/34 606/87 |
| 2012/0130382 A1 | 5/2012 | Iannotti et al. | |
| 2012/0245587 A1 | 9/2012 | Fang et al. | |
| 2013/0053854 A1 | 2/2013 | Schoenefeld et al. | |
| 2013/0123850 A1 | 5/2013 | Schoenfeld et al. | |
| 2013/0218163 A1 | 8/2013 | Frey | |
| 2014/0074099 A1 | 3/2014 | Vigneron et al. | |
| 2014/0163565 A1 * | 6/2014 | Bollinger | A61B 17/1746 606/91 |
| 2014/0358152 A1 | 12/2014 | Condino et al. | |
| 2015/0320430 A1 * | 11/2015 | Kehres | A61B 17/1739 606/87 |
| 2018/0042619 A1 | 2/2018 | Frey et al. | |
| 2018/0177512 A1 | 6/2018 | Hogan et al. | |
| 2021/0077119 A1 | 3/2021 | Siccardi et al. | |
| 2021/0077130 A1 | 3/2021 | Siccardi et al. | |

FOREIGN PATENT DOCUMENTS

| | | |
|---|---|---|
| DE | 102016218965 | 4/2018 |
| EP | 2502582 | 9/2012 |
| EP | 2749235 | 7/2014 |
| JP | 2015208566 A | 11/2015 |
| JP | 2016524506 | 8/2016 |
| JP | 6324194 B2 * | 5/2018 |
| TW | 200908927 | 3/2009 |
| TW | 201 238 556 | 10/2012 |
| WO | 9600049 | 1/1996 |
| WO | 2012/156466 A1 | 11/2012 |
| WO | 2013158521 | 10/2013 |
| WO | 2014070889 | 5/2014 |
| WO | 2014090908 | 6/2014 |
| WO | 2014197844 | 12/2014 |
| WO | 2016075581 | 5/2016 |
| WO | 2016075660 | 5/2016 |
| WO | 2018055494 | 3/2018 |
| WO | 2018055518 | 3/2018 |

OTHER PUBLICATIONS

International Search Report and Written Opinion, issued by the International Searching Authority (ISA/EP) in Application No. PCT/IB2018/060160 dated Apr. 5, 2019. 13 pages.

Berry et al., Personalised image-based templates for intra-operative guidance, Proceedings of the Institution of Mechanical Engineers, Part H: Journal of Engineering in Medicine, vol. 219, pp. 111-118, 2004.

Brussel et al., Medical Image-Based Design of An Individualized Surgical Guide for Pedicle Screw Insertion, 18th Annual International Conference of the IEEE Engineering in Medicine and Biology Society, Amsterdam, pp. 225-226, 1996.

Lu et al., A novel computer-assisted drill guide template for placement of C2 laminar screws, Eur Spine J, vol. 18, pp. 1379-1385, 2009.

Lu et al., A Novel Patient-Specific Navigational Template for Cervical Pedicle Screw Placement. Spine, vol. 34, No. 26, pp. E959-E964, 2009.

Lu et al., Rapid prototyping drill guide template for lumbar pedicle screw placement, Chinese Journal of Traumatology, vol. 12(3), pp. 171-177, 2009.

Popescu et al., Design and Rapid Manufacturing of Patient-Specific Spinal Surgical Guides: A Survey, Proceedings in Manufacturing Systems, vol. 7, Issue 2, pp. 115-120, 2012.

Radermacher, Klaus, Computer Assisted Orthopaedic Surgery with Individual Templates, Helmholtz-Institute for Biomedical Engineering, 2 pages, 1997.

Ryken et al., Image-based drill templates for cervical pedicle screw placement, J Neurosurg Spine vol. 10, pp. 21-26, 2009.

English Translation of Notice of Reasons of Refusal in JP 2019-536354, dated Feb. 10, 2020, 7 pages.

International Search Report and Written Opinion issued for Application No. PCT/IB2017/055688. dated Nov. 16, 2017. 11 pages.

International Search Report and Written Opinion issued for Application No. PCT/IB2017/055588. dated Nov. 22, 2017. 13 pages.

English Translation of Notice of Reasons of Refusal in JP 2019-536348, dated Feb. 27, 2020, 14 pages.

International Search Report and Written Opinion issued for Application No. PCT/IB2019/053765 dated Aug. 6, 2019. 15 pages.

International Search Report and Written Opinion, issued by the International Searching Authority (ISAEP) in Application No. PCT/IB2018/060161 dated Apr. 5, 2019. 9 pages.

International Search Report and Written Opinion for International Application No. PCT/IB2019/058162 dated Jan. 22, 2020. 16 pages.

Office Action issued for U.S. Appl. No. 16/333,057, dated Jul. 30, 2020.

Office Action issued for U.S. Appl. No. 16/333,055, dated Dec. 8, 2020.

International Search Report and Written Opinion, issued by the International Searching Authority (ISAEP) in Application No. PCT/IB2019/060161 dated Apr. 2, 2020. 11 pages.

Office Action issued for U.S. Appl. No. 16/956,253, dated Oct. 12, 2021.

Office Action issued for U.S. Appl. No. 17/281,900 dated Dec. 2, 2021.

Notice of Allowance received in connection with U.S. Appl. No. 16/956,253, dated Feb. 8, 2022, 10 pages.

* cited by examiner

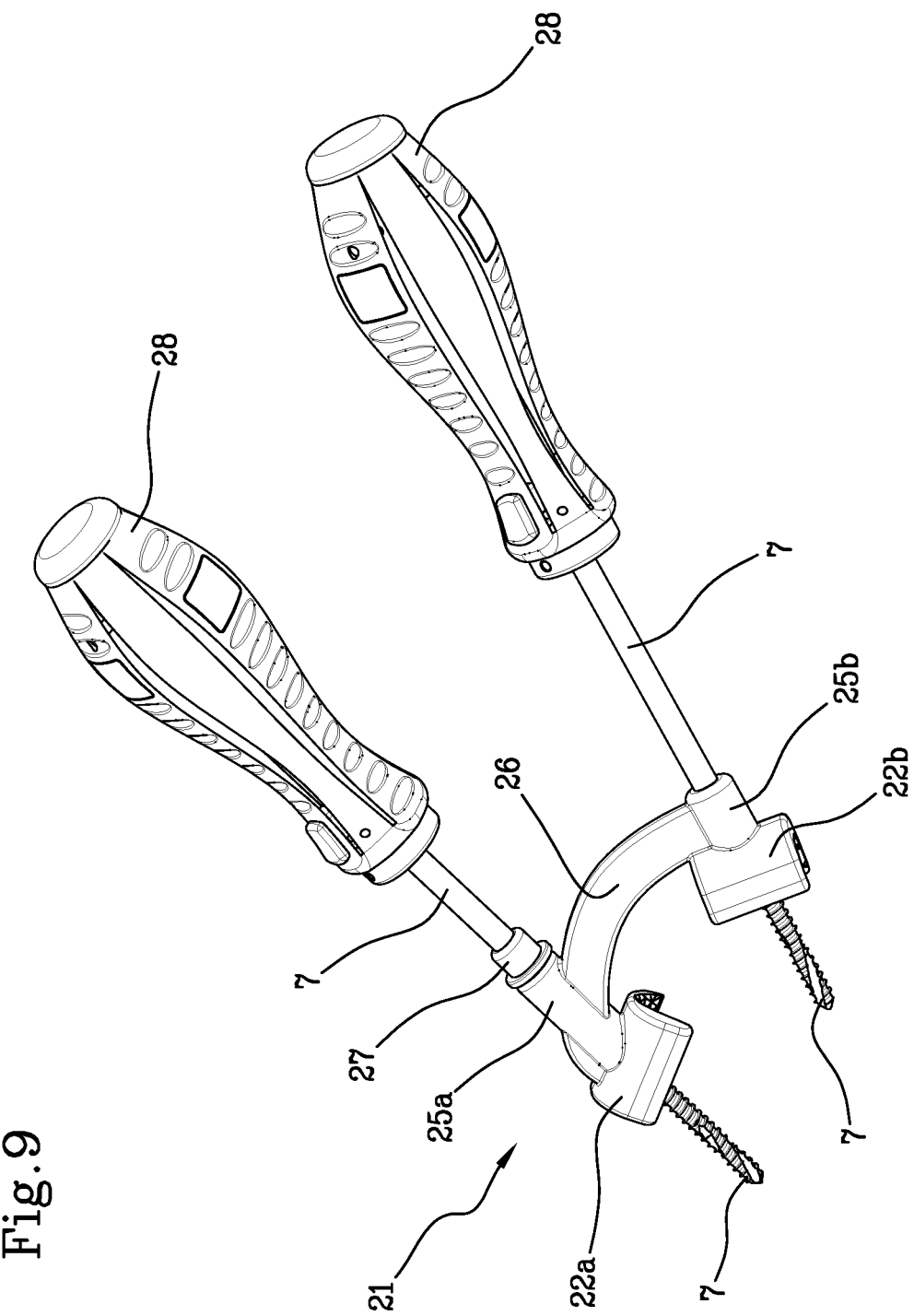

_US 11,602,355 B2_

CUTTING GUIDE FOR PERIACETABULAR OSTEOTOMY AND KIT FOR PERIACETABULAR OSTEOTOMY

The present invention relates to a cutting guide for periacetabular osteotomy.

Periacetabular osteotomy is a surgical procedure that has to be performed to treat hip dysplasia, a condition in which the hip joint develops abnormally so that the head of the femur gradually becomes dislodged from the acetabulum.

The hip joint is formed by the acetabulum and the head of the femur. When hip dysplasia occurs, the head of the femur does not fit firmly in the acetabulum and easily becomes dislocated. Thus, the two parts (concave and convex) of the joint do not fit together perfectly and this can result in a state of general instability of the articular system, making the hip very susceptible to dislocation.

Periacetabular osteotomy, or PAO, is a highly specialised procedure that has evolved over many years, the aim of which is to realign the acetabulum in order to restore the physiological morphology of the joint.

The objective of surgical treatment of dysplasia is to restore congruency of the joint and thus normal biomechanical forces: periacetabular osteotomy is performed to increase the area of contact, reduce instability-related stress and normalise load forces.

Periacetabular osteotomy involves cutting the bone around the acetabulum and detaching it completely from the hip bone, without interrupting the continuity of the bone between the upper part and the lower part of said hip bone. In other words, it consists in creating a fracture in the deformed bone between the hip bone and the acetabulum in order to separate the bone into two parts. The acetabulum fragment is then translated and redirected so that the acetabulum is in the correct position, and then fixed in place using screws and metal wire.

When performed by experienced surgeons, this highly specialised surgical procedure produces excellent clinical, radiographic and functional results, by realigning the two parts of the bone in a new and mechanically correct position.

This method currently involves a number of osteotomies around the joint, in order to completely free the acetabulum so that it can be redirected and fixed in the best position.

However, all cutting is done freehand by the surgeon, following a line determined in advance in the preoperative stage.

This method of cutting clearly involves difficulties and carries some risks for the patient, as the success of the operation depends entirely on the experience and skill of the surgeon.

Owing to the vibrations caused by the bone cutting instrument, there is always a risk of not following the cut properly or of touching soft tissue.

Once the osteotomies are complete, the acetabular fragment is completely mobile and is redirected in order to gain the required lateral coverage and angle of version under intraoperative image intensifier control.

Therefore, the two parts into which the bone has been cut are also rotated and realigned by sight, and the surgeon rotates the acetabulum until gaining the correct alignment by examining antero-posterior projections of the entire pelvis during the surgical procedure.

There is certainly also a high risk of human error during the realignment step.

The purpose of the present invention is therefore to provide a cutting guide for periacetabular osteotomy that assists the surgeon during the cutting step, reducing the risks for the patient due to human error to a minimum and shortening operating times.

A further purpose of the present invention is to provide a cutting guide for periacetabular osteotomy that defines and clearly indicates the cutting line to the surgeon in order to achieve an accurate cut without the risk of touching soft tissue or deviating from the predefined cutting line.

Yet another purpose of the present invention is to propose a kit for performing periacetabular osteotomy that not only makes it possible to achieve an accurate cut but also a correct realignment of the two parts into which the bone has been cut according to the physiological morphology of the joint.

These and further characteristics, and the respective advantages, of a cutting guide for periacetabular osteotomy and a kit for periacetabular osteotomy will be more apparent from the description that follows of a preferred and non-exclusive embodiment represented solely by way of non-limiting example in the accompanying figures, in which:

FIG. 9 illustrates the aligner of FIG. 8 detached from the bone to be cut, in order to more clearly show all of its parts.

Figure 1:
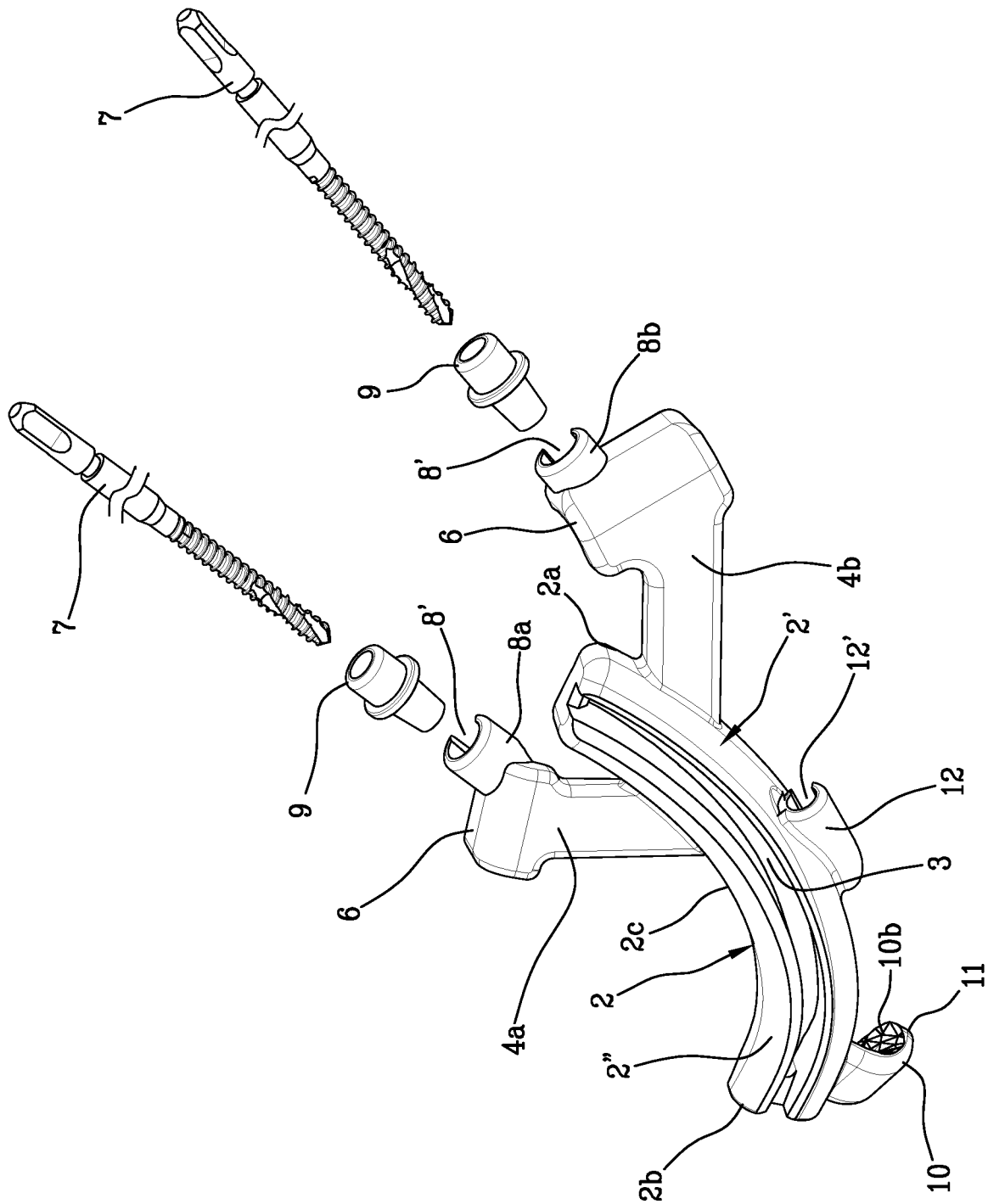
FIG. 1 is a perspective view from above of a first main body of a cutting guide for periacetabular osteotomy according to the present invention.

In the accompanying figures, reference numeral 1 globally denotes a cutting guide for periacetabular osteotomy, according to the present invention.

Figure 7:
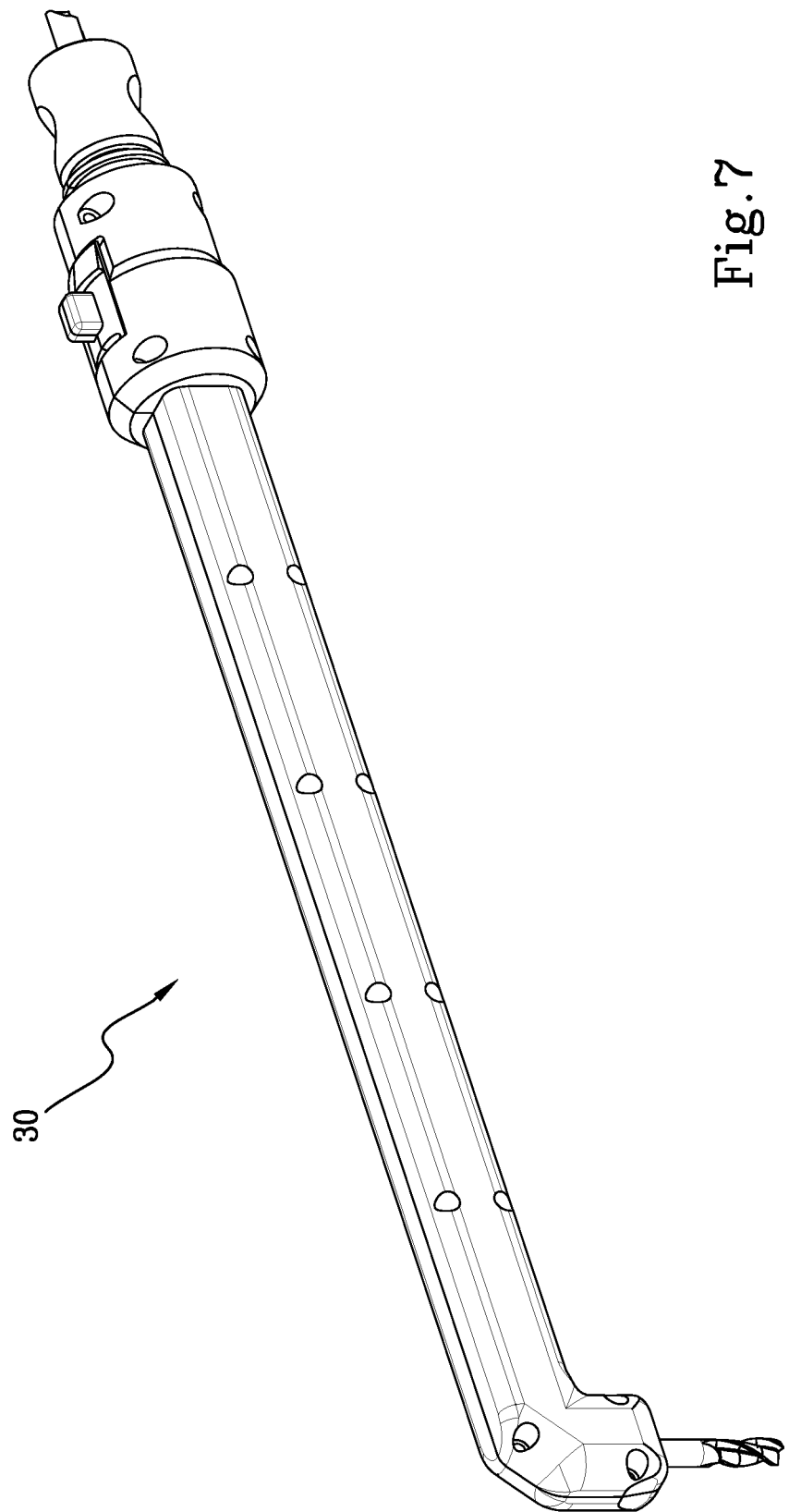
FIG. 7 illustrates a bone cutting instrument.

The cutting guide 1 is a device used to assist the surgeon during an operating step, in particular during the cutting of the bone B, by defining a univocal cutting path to be followed by the bone cutting instrument 30 (FIG. 7).

The cutting guide 1 comprises at least a first main body 2 (FIGS. 1 and 2) having a longitudinal opening 3 for the insertion of a cutting instrument 30. This first main body 2 may also be referred to as the proximal guide.

Said longitudinal opening 3 essentially extends from a first end 2a to a second end 2b of the first main body 2 along the longitudinal axis of extension of the first main body 2.

Said opening 3 is such that when the proximal guide 2 is coupled to the bone, the underlying bone is visible through it.

The first main body 2 has a first portion 2' that extends from the first end 2a to an intermediate section 2c, and a second portion 2" that extends from the intermediate section 2c to the second end 2b.

The cut to be performed along the bone is not rectilinear but must follow a periacetabular osteotomy path: for that reason the first main body 2, which comprises the longitudinal opening 3 that follows the cutting line, is not rectilinear, but has a curvilinear shape. Likewise, the opening 3 follows the exact curvilinear shape of the periacetabular osteotomy path.

The first main body 2 comprises, in correspondence with the first portion 2', at least two positioning and fixing arms 4a and 4b, extending away from the first main body 2. Each arm 4a and 4b extends away from the first main body 2 towards the first end 2a, from opposite sides with respect to the longitudinal opening 3.

The purpose of said arms 4a and 4b is to correctly position the cutting guide 1, in particular the first main body 2 of the guide 1, on the bone B to be cut. Both the first main body 2 and the positioning and fixing arms 4a, 4b have a lower surface 5, i.e., the surface that is coupled to the patient's bone, shaped on the anatomy of the patient's bone to enable the correct and univocal positioning thereof. In other words, the lower surface 5 is the negative of the surface of the bone to which the first main body 2 must be coupled.

In addition, the positioning and fixing arms 4a, 4b have at least one fastener lip 6 suitable to grasp an edge of the bone to be cut and having lower edges shaped so that, like the lower surface 5, they are shaped on the anatomy of the patient.

Each positioning and fixing arm 4a, 4b is coupled to a respective fastening member 7 for fixing it to the bone to be cut.

Figure 3:
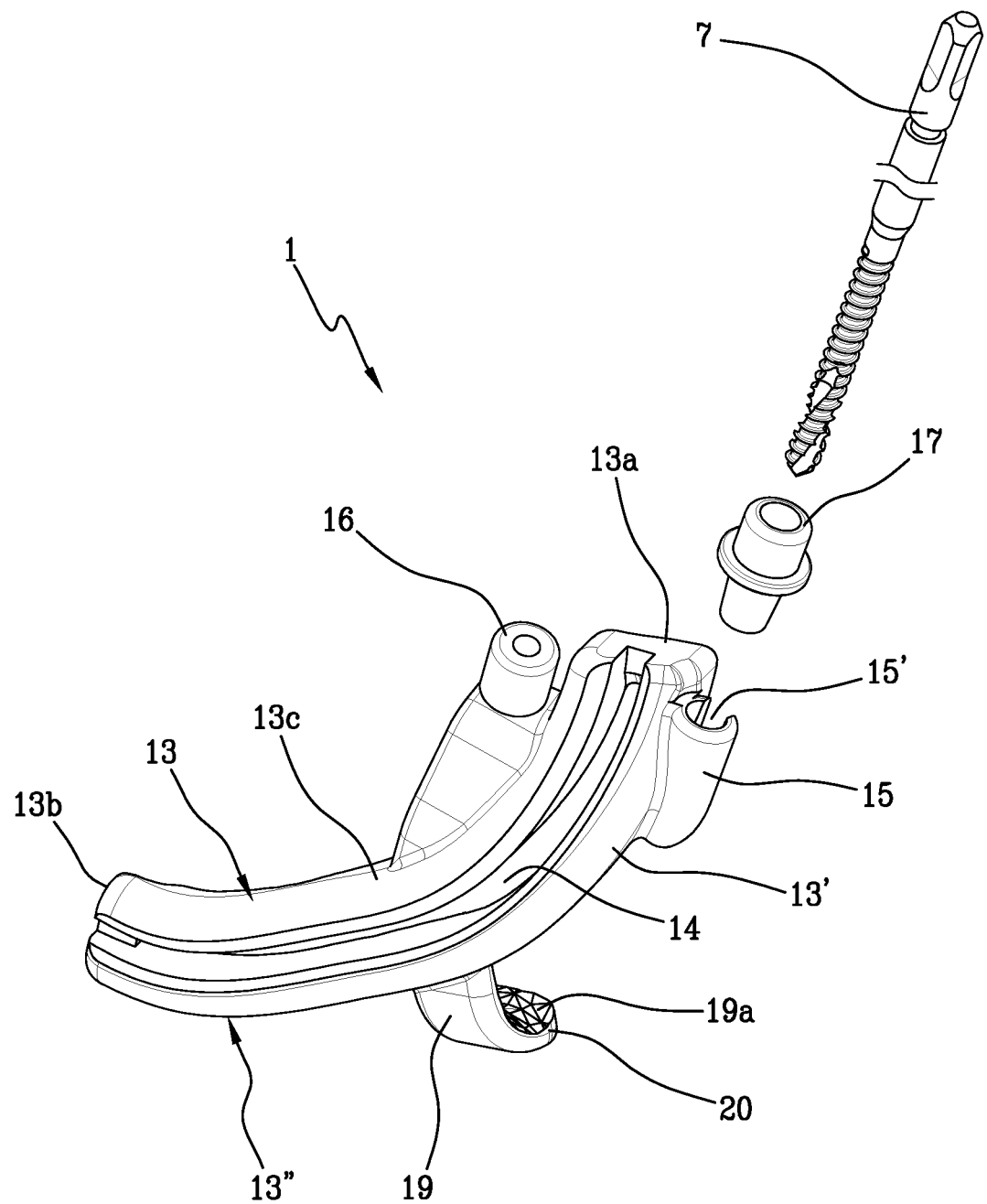
FIG. 3 is a perspective view from above of a second main body of a cutting guide for periacetabular osteotomy according to the present invention.

A typical fastening member is, for example, a surgical screw, a pin, or a cortical screw (Schanz screw), as can be seen in FIGS. 1, 3 and 9.

The fastening members 7 to which the first main body 2 is coupled are only illustrated in certain positions.

Specifically, each positioning and fixing arm 4a, 4b comprises a respective sleeve, a first sleeve 8a and a second sleeve 8b, into which a respective fastening member 7 can be inserted.

Figure 2:
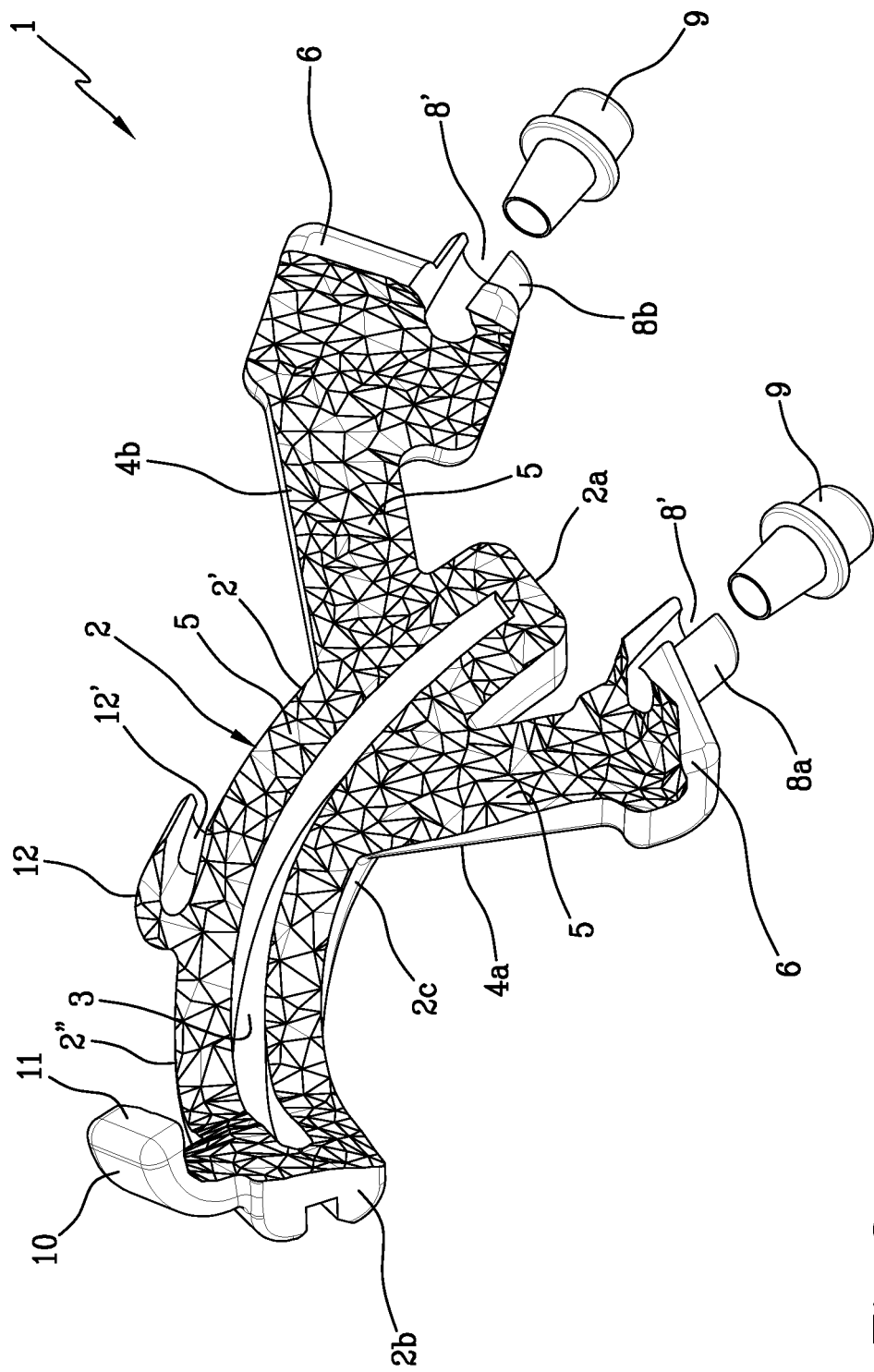
FIG. 2 is a perspective view from below of the first main body of a cutting guide for periacetabular osteotomy illustrated in FIG. 1.

As shown in FIGS. 1 and 2, the sleeves 8a, 8b protrude from the respective arms 4a, 4b with a collar.

To achieve a stable connection between the first main body 2 and the fastening members 7, there are bushings 9 that can be fitted over each sleeve 8a, 8b in correspondence with the respective collars.

This additional connection serves to achieve a more secure fastening of the structure, and thus of the proximal guide or first main body 2 to the fastening member 7 so as to limit the vibrations transmitted by the cutting instrument to the entire device with the subsequent risk of misalignment of the guide.

The first sleeve 8a and the second sleeve 8b each have a side opening 8', to allow the disengagement of the first main body 2 from the fastening members 7. Therefore, the first sleeve 8a and the second sleeve 8b of the first main body 2 have a substantially C-shaped cross section.

The fastening members 7 remain inserted in the bone until the end of the operation, whereas the first main body 2 must be removed during the operation. For this reason, to remove the first main body 2 from the fastening members 7 without causing any misalignment or shifting of the bone and/or of the screws, the first main body 2 is moved away from the bone by passing the shank of the fastening members 7 through the side opening 8' obtained along the axial extension of each sleeve 8a and 8b.

The first main body 2 further comprises a positioning pin 10 projecting from and arranged in proximity to the second end 2b of the first main body 2.

The purpose of said pin 10, like the arms 4a and 4b, is to correctly position the first main body 2 on the bone to be cut and make it possible to grip the bone firmly. To provide a stable and univocal connection, the pin 10 has a lower surface 10b, the one that abuts against the bone, shaped on the anatomy of the patient's bone; furthermore, the pin also comprises at least one fastener lip 11, which is also shaped on the anatomy of the patient, that grasps an edge of the bone to be cut.

Along its longitudinal extension, essentially in correspondence with the intermediate section 2c, the first main body 2 has a third sleeve 12 (visible in FIGS. 1 and 2) suitable for the insertion of a respective third fastening member 7, so as to achieve a third point for connecting the first main body 2 to the bone to be cut.

As can be seen in FIGS. 1 and 2, the third sleeve 12 also has a side opening 12' to allow the disengagement of the first main body 2 from the respective fastening member 7 inserted in the third sleeve 12. Also in this case, the fastening member 7 inserted in the third sleeve 12 remains in place in the bone even after the first main body 2 has been removed. It must therefore be possible to separate the latter from the fastening screw easily and without causing any misalignment of the screw or of the partially cut bone.

The cutting guide 1 according to the present invention further comprises a second main body 13 (FIGS. 3 and 4), which also has a longitudinal opening 14 for the insertion of the same cutting instrument 30 previously used with the first main body 2.

This second main body 13 may also be referred to as the distal guide.

The second main body 13 also has a first portion 13' that extends from a first end 13a to an intermediate section 13c of the second main body 13, and a second portion 13" that extends from this intermediate section 13c to a second end 13b of the second main body 13.

The longitudinal opening 14 of the second main body 13 extends from the first end 13a to the second end 13b of the second main body 13.

The second main body 13 also has a curvilinear shape to follow the path of the cut to be made along the bone, and thus to follow the periacetabular osteotomy path.

Therefore, the longitudinal opening 14 of the second main body 13 is not rectilinear either, but has a curvilinear shape to follow the exact periacetabular osteotomy path.

Figure 4:
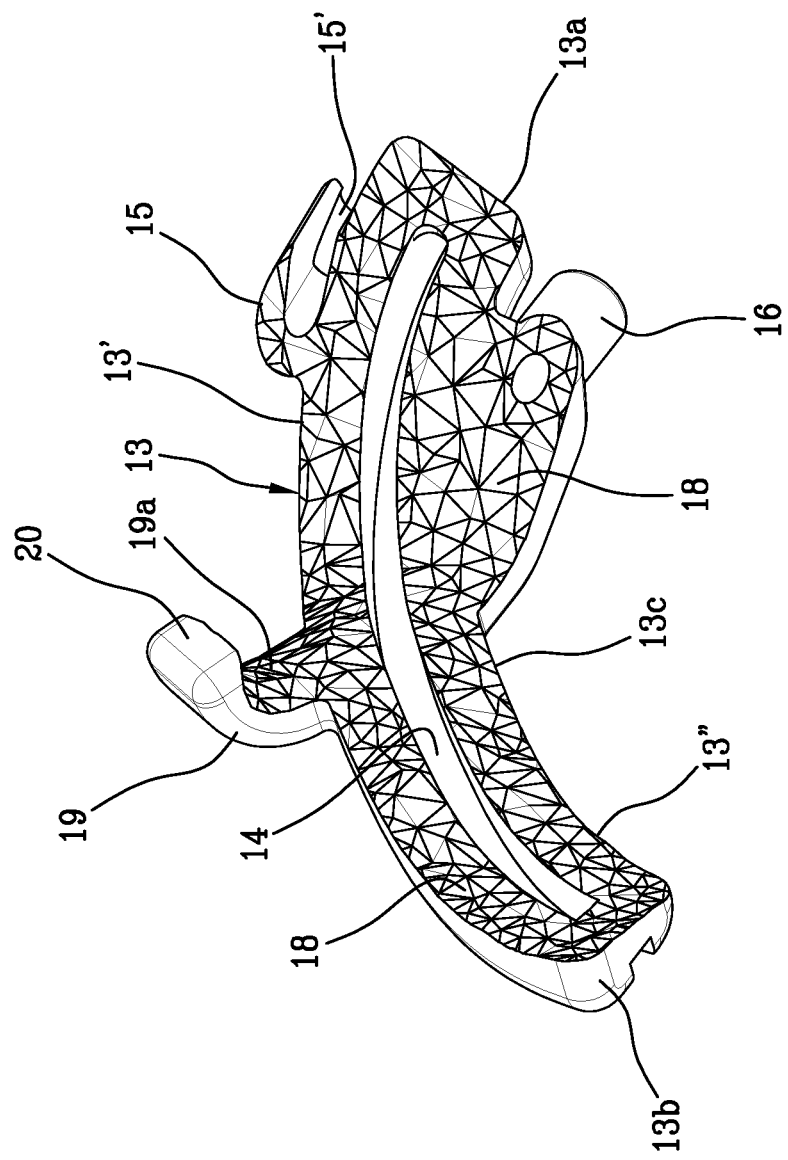
FIG. 4 is a perspective view from below of the second main body of a cutting guide for periacetabular osteotomy illustrated in FIG. 3.
Figure 5:
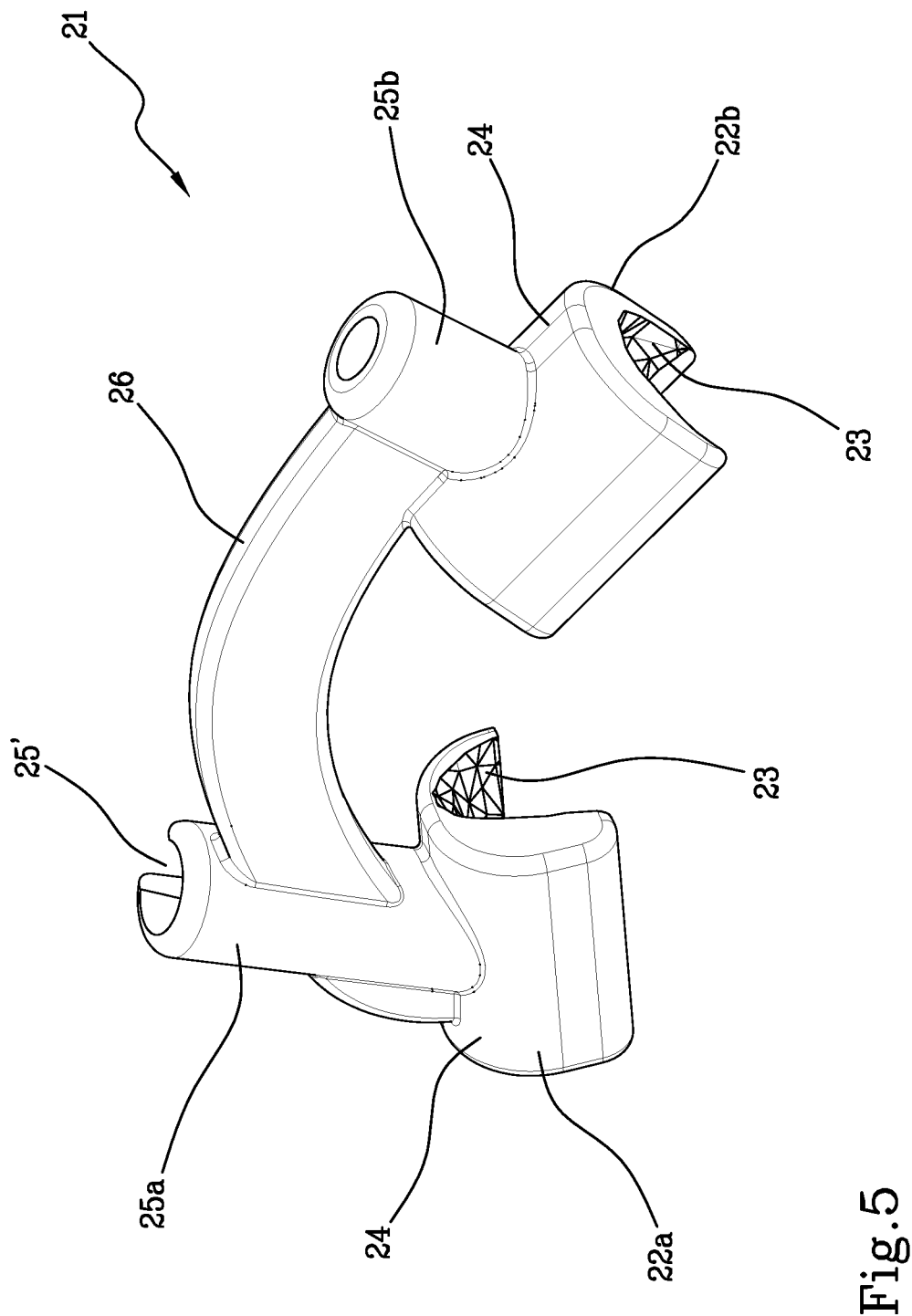
FIG. 5 is a front perspective view of an aligner included in a kit for periacetabular osteotomy.

As can be seen in FIGS. 3 and 4, the second main body 13 has a first portion 13' that is superimposable on the second portion 2" of the first main body 2.

The partial superimposition of the two guides, namely of the proximal and distal guides, is due to the sequence in which the two guides are used during the surgical procedure: the first part of the cut is performed using the first main body 2 (proximal guide) as the guide, and thus as the template for the cutting instrument, whereas the second part of the cut is performed using the second main body 13 (distal guide) as the cutting template. When the proximal guide used to make the first part of the cut has been removed and the distal guide has been fitted, there is a partial superimposition of the first portion 13' of the second main body 13 and the second portion 2" of the first main body 2, in order to ensure that the surgeon continues to make the cut correctly. In other words there is a partial superimposition of the longitudinal opening 14 of the second main body 13 and the cut that has already been made, in particular of the first part of the longitudinal opening 14 of the second main body 13 and the final part of the cut that has already been made and created in correspondence with the second portion 2" of the first main body 2. Following on from this partial superimposition, the longitudinal opening 14 of the second main body 13 continues the exact cutting line along the periacetabular osteotomy path, to complete the cutting of the entire bone.

The second main body 13 has a first sleeve 15, suitable for the insertion of a respective fastening member 7, arranged in proximity to the first end 13*a* of the second main body 13.

The first sleeve 15 of the second main body 13 has a side opening 15' to allow the disengagement of the second main body 13 from the respective fastening member 7 inserted in the first sleeve 15.

This opening permits the fast and secure connection of the second main body 13 to the fastening member 7 already in place in the bone.

In actual fact, the first sleeve 15 of the second main body 13 is coupled to the fastening member 7 that was previously inserted in the third sleeve 12 of the first main body 2. As mentioned above, this is because the first portion 13' of the second main body 13 is superimposable on the second portion 2" of the first main body 2.

Furthermore, the second main body 13 has a second sleeve 16, suitable for the insertion of a respective fastening member 7, arranged in proximity to the first end 13*a* of the second main body 13.

This second sleeve 16 is closed, and so, unlike the sleeves described previously, does not have a side opening.

To achieve a stable connection between the second main body 13 and the respective fastening member 7 inserted in the first sleeve 15, a bushing 17 is fitted over the sleeve 15.

As mentioned above, while the fastening member 7 that can be coupled to the first sleeve 15 of the second main body 13 is the same fastening member 7 that was previously coupled to the third sleeve 12 of the first main body 2, the fastening member 7 inserted in the second sleeve 16 of the second main body 13 is a cortical screw exclusively dedicated to the second main body 13.

In order for the second main body 13 to be stably and univocally coupled to the bone to be cut, the lower surface 18 of the second main body 13, that is to say, the surface that faces and is coupled to the bone, is shaped on the anatomy of the patient's bone and thus follows the negative of the surface of the bone.

For greater stability and a more correct positioning of the second main body 13 on the bone to be cut, there is also a positioning pin 19 that extends from the second main body 13 in correspondence with the intermediate section 13*c* of the second main body 13.

The positioning pin 19 further comprises a fastener lip 20 to grasp an edge of the bone to be cut, and has a lower surface 19*a* that is coupled directly to the bone, shaped on the anatomy of the patient's bone, to permit the correct positioning of the second main body 13.

The present invention also relates to a kit for periacetabular osteotomy comprising a cutting guide 1 according to that described above, at least two fastening members 7, for example surgical screws, pins or cortical screws (Schanz screws), that can be coupled to the cutting guide, at least in a first operating step, and an aligner 21 that can be coupled to said two fastening elements 7 in at least a second operating step.

Figure 8:
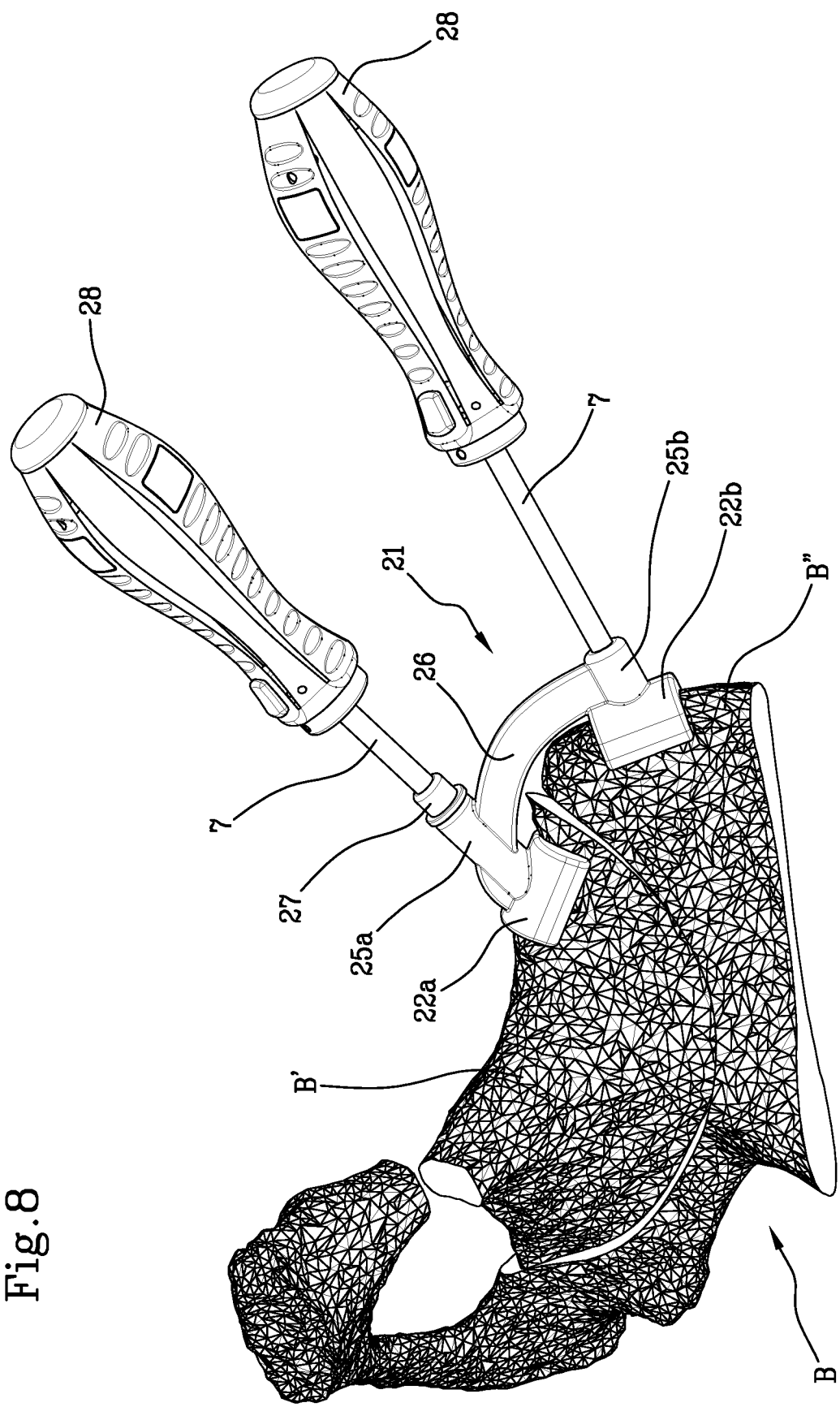
FIG. 8 illustrates the aligner of FIGS. 5 and 6 in an operating step, connected to a bone to be cut and to two handles for realigning the bone.

Said aligner 21 (FIGS. 6, 8 and 9) comprises a first 22*a* and a second 22*b* resting base, each shaped on the patient's anatomy and each suitable to rest on a respective part in which the bone has been cut.

Each resting base 22 can be coupled to at least said two fastening elements 7.

In more detail, each resting base 22*a*, 22*b* has a substantially C-shaped cross section, with the concave side that can be coupled to the bone.

The surface 23 of the concave side of each base 22*a*, 22*b* is shaped on the patient's specific anatomy, and is thus the negative of the surface of the bone to which it is to be coupled.

On the convex side 24 of each base 22*a*, 22*b* there is a sleeve 25*a*, 25*b* that projects upwards from the respective base 22*a*, 22*b*.

Figure 6:
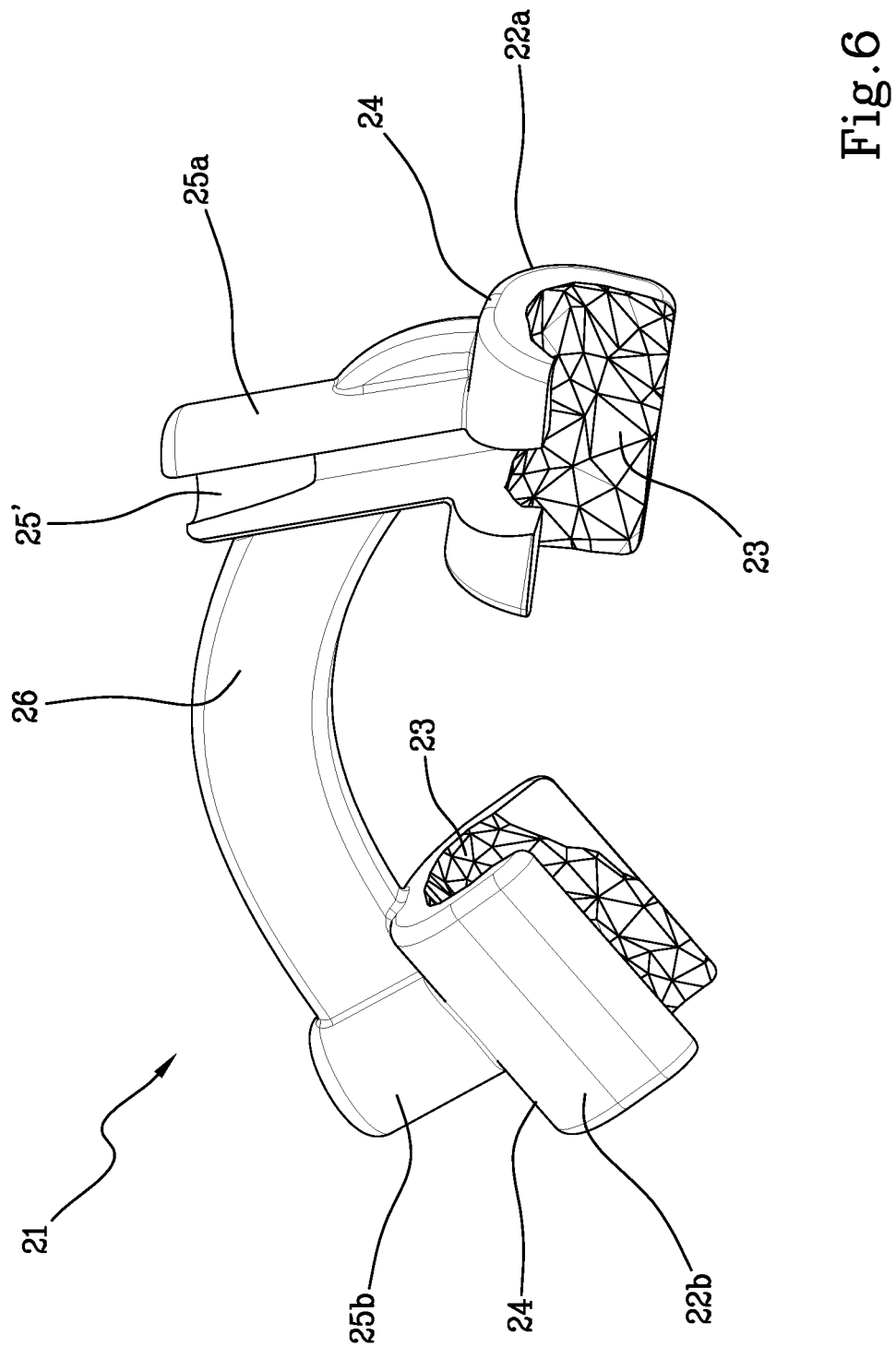
FIG. 6 is a rear perspective view of the aligner shown in FIG. 5.

A first sleeve 25*a* has a side opening 25' that also extends along the respective first base 22*a*, as can be seen in FIG. 6.

The second sleeve 25*b*, instead, has no side openings but is axially hollow for the insertion of a respective fastening member 7.

A bushing 27 can be coupled to this second sleeve 25*b* in order to achieve a stable connection between the aligner 21 and the fastening member 7.

The aligner 21 further comprises a connecting bridge 26 or an arched structure, which connects the resting bases 22*a*, 22*b* and, in particular, connects the two sleeves 25*a* and 25*b*.

This connecting bridge 26 is shaped on the basis of the new and correct position that the two parts B', B" into which the bone has been cut must have with respect to one another. In other words, the connecting bridge 26 has a length, and thus a distance between the resting bases 22*a*, 22*b*, and a mutual inclination between said resting bases 22*a*, 22*b* defined on the basis of the final arrangement that the two parts B', B" into which the bone has been cut must have in the correct and final anatomical position. The shape of the aligner 21 is also defined and established in the preoperative planning stage.

The sleeves 25*a* and 25*b* of the aligner are coupled to the fastening members 7 that, during the first operating cutting step, were coupled to the first sleeve 8*a* and the second sleeve 8*b* of the first main body 2.

The kit for periacetabular osteotomy further comprises a pair of handles 28 suitable to be fitted over the fastening members 7 inserted in the first sleeve 25*a* and the second sleeve 25*b* of the aligner 21.

Said handles 28 are used to firmly grip and manoeuvre the aligner 21, acting directly on the fastening members 7 connected to the aligner via the sleeves 25*a* and 25*b* and the bushing 27.

In this way, the two parts of the bone can be correctly positioned and moved with respect to one another.

During the operating step, the first main body 2 is positioned on the bone to be cut in a univocal and predetermined position, not only by means of the lower surface 5 but also the positioning and fixing arms 4*a*, 4*b*, each provided with the fastener lip 6.

Once the first main body 2 has been positioned, the fastening members 7 are inserted in the sleeves 8*a*, 8*b* of the arms 4*a* and 4*b*. The first main body 2 is then stably fixed to the fastening members 7 by means of the bushings 9.

The first main body 2 is fixed to the bone by means of a third fastening member 7 inserted in the third sleeve 12 arranged in correspondence with the intermediate section 2*c* of the second main body 2.

With the first main body 2 thus secured to the bone to be cut, the actual cut can be made using a bone cutting instrument 30.

The latter is generally a bone cutter, better illustrated in FIG. 7, that is inserted into the opening 3 of the first main body 2.

The bone cutter is thus guided by said opening 3 to cut the bone along the exact periacetabular osteotomy path defined in the preoperative stage.

The cutting instrument 30 thus follows the entire opening, from the first end 2a to the second end 2b of the first main body 2. The first part of the bone is thus cut.

When the first cut has been completed, the cutter 30 is moved away from the patient's body, and the bushings 9 are removed to allow the disengagement of the first main body 2 from the fastening members 7.

Specifically, the fastening members 7 inserted in the sleeves 8a, 8b of the arms 4a and 4b, must remain in place and not be removed until the end of the operation. The fastening member 7 inserted in the third sleeve 12 must also remain in place, at least until the cut is complete: in other words, the fastening member 7 inserted in the third sleeve 12 must also remain in the bone during the second part of the cut that is performed with the second main body 13 or distal guide coupled to the bone.

The angle at which the fastening members 7 are inserted into the bone is established by the inclination of the sleeves 8a and 8b with respect to the first main body 2.

Said inclination is determined by the need to fix said fastening members 7 stably to the bone structure, without damaging the latter and so as to create the largest possible area of interaction between the bone and the fastening members; for these reasons it is defined in the preoperative planning stage, on the basis of the bone anatomy.

The main body 2 is removed from the position in which it is coupled to the bone through the side openings 8' obtained along the sleeves 8a and 8b and the opening 12' along the third sleeve 12.

The first main body 2 is thus used to make the first part of the cut, which must be completed using the second main body 13. After removing the first main body 2, the second main body 13 must be positioned.

In particular, to ensure the correct alignment of the distal guide and be able to continue cutting in the right direction, said guide has a first portion 13' that is superimposable on the second portion 2" of the proximal guide 2.

In actual fact, the fastening member 7 that was previously inserted in the third sleeve 12 and is still fixed to the bone is used to connect it to the first sleeve 15 of the second main body 13.

The positioning pin 19 of the distal guide 13 is arranged exactly where the positioning pin 10 of the proximal guide 2 was attached.

When the second main body 13 is in place, a new fastening member 7, the fourth, is inserted in the second sleeve 16, using the third fastening member 7 and the positioning pin 19 as references.

A connecting bushing 17 is connected to the second sleeve 16 to connect the fastening member securely to the second main body 13, in order to prevent the vibrations transmitted by the cutter from causing any movement of said distal guide.

The actual cut is then made, by inserting the bone cutting instrument 30 into the longitudinal opening 14, from the first end 13a to the second end 13b. Once the second part of the cut is also complete, the second main body 13 is removed by separating the bushing 17 from the second sleeve 16 and then extracting the fastening member 7 from inside the second sleeve 16. The second main body 13 can thus be removed from the surgical site. Lastly, the fastening member 7 coupled to the first sleeve 15 can be extracted. The next step of the surgical procedure consists in realigning the two parts B', B" into which the bone has been cut so that they assume the correct anatomical position, as described later on.

Two fastening members 7 remain fixed inside the bone, in particular, the first two that were inserted in the first sleeve 8a and the second sleeve 8b, respectively, of the first main body 2 or proximal guide.

Each fastening member 7 is inserted in one of the two parts B', B" into which the bone has been cut.

For the second operating step, in which the bone is realigned, the aligner 21 must be connected to the fastening members 7.

The aligner 21, in particular the second sleeve 25b, is fitted over one of the two fastening members 7 from the top, while the other fastening member 7 is inserted in the first sleeve 25a, through the side opening 25'.

The geometry of the aligner 21 is defined in advance in the preoperative planning stage and defines the mutual position that the fastening members 7 must have in the configuration in which the two parts B', B" into which the bone has been cut are correctly aligned. In other words, once the aligner 21 has been coupled to the fastening members 7, each of which, in turn, has been inserted into one of the two parts B', B" into which the bone has been cut, it will force the fastening members 7, and thus the two parts of bone, to rotate with respect to one another to assume the correct final position. The aligner 21, in particular the connecting bridge 26, is rigid, and therefore cannot be deformed, and will force the two parts B', B" of the bone to move with respect to one another to comply with the geometry set by the aligner. To do this, once the second sleeve 25b has been connected to one of the two fastening members 7, the handles 28 are fitted over each fastening member 7 in order to be able to rotate the two parts B', B" of bone and bring the other fastening member 7 that is still free in proximity to the side opening 25' of the first sleeve 25 of the aligner 21.

The fastening member 7 is then inserted in the first sleeve 25a through the side opening 25'.

The handle 28 positioned on this fastening member 7 is removed in order to fit the bushing 27 on the first sleeve 25a and stably connect the fastening member 7 to the aligner 21.

The first sleeve 25a has a collar that protrudes upwards with respect to the connecting bridge 26: the bushing 27 is coupled to this collar.

With the fastening members 7 thus connected to the aligner 21, any necessary final adjustments are then made to the alignment and to the relative rotation of the two parts B', B" into which the bone has been cut, to comply with the geometry of the connecting bridge 26 of the aligner 21.

When the two portions of the bone are aligned and the final relative position of the two parts B' and B" has been defined, connecting screws are inserted between the two parts into which the bone has been cut to block them and stabilise their position and relative rotation.

Lastly, the handles 28, the bushing 27 and the entire aligner 21 are removed and then the two fastening members 7.

The invention brings notable advantages with respect to the current operating technique that, as mentioned above, does not envisage the use of a cutting guide, but cutting the bone freehand using bone cutters.

The present invention, on the other hand, proposes a cutting guide in order to perform cutting accurately and safely, which is of considerable help to the surgeon during the operating step in that it defines a previously established cutting path.

The cutting guide, as presented in the present description, actually envisages two cutting guides that are used in sequence. However, it can envisage a single cutting guide defining the entire path of the cut to be made.

The surgeon simply has to position the guide, the lower surface of which is the negative of the bone to which it must be coupled, and fix it to the bone using appropriate fastening members.

Once the guide has been stably connected to the bone, the surgeon only has to insert the bone cutting instrument, for example the cutter, into the channel or central opening obtained longitudinally along the guide. This opening follows the cutting path defined in the preoperative stage: the cutter is made to slide and move along said opening to cut the bone accurately and safely without any risk for the patient.

After making the cut, the aligner is used to move the two portions of bone and force them to assume the correct alignment. The surgeon is again assisted in this second operating step and has an instrument that enables him or her to achieve the most correct alignment, without merely having to rely on a visual evaluation made on the spot, which could also be difficult owing to the presence of blood or soft tissue obstructing the view of the surgical site.

When the kit for periacetabular osteotomy is used, the risk of error is reduced to a minimum, the cut is easier for the surgeon to perform and the acetabulum is more accurately realigned in accordance with the preoperative plan, operating times are significantly shortened, the operation is less invasive for the patient and the overall success rate for the operation improves.

The invention claimed is:

1. A kit for periacetabular osteotomy, the kit comprising:
a cutting guide,
a plurality of fastening members configured to be inserted in said cutting guide in a first operating step, and
an aligner,
wherein the cutting guide comprises:
at least a first main body having a longitudinal opening defining a cutting line for insertion of a cutting instrument, the longitudinal opening extending from a first end to a second end of said first main body, said first main body has a first portion extending from said first end to an intermediate section and a second portion extending from said intermediate section to said second end;
at least two positioning and fixing arms, the at least two positioning and fixing arms extending away from said first main body from opposite sides with respect to said longitudinal opening, the at least two positioning and fixing arms being adapted to correctly position said first main body on a bone to be cut and fix the first main body thereto through at least two of said plurality of fastening members; and
a second main body having a longitudinal opening defining a cutting line for insertion of the cutting instrument, the longitudinal opening of the second main body extending from a first end to a second end of said second main body, wherein said second main body has a first portion extending from the first end to an intermediate section of said second main body, and a second portion extending from said intermediate section to said second end of said second main body, wherein the second main body is formed separately from the first main body,
wherein said first portion of said second main body has substantially the same shape as the second portion of said first main body such that, when replacing the first main body with the second main body, the cutting line defined by the longitudinal opening of the second main body continues the cutting line defined by the longitudinal opening of the first main body, wherein the cutting instrument is configured to cut the bone into two bone parts,
wherein said aligner comprises a first resting base and a second resting base, each resting base having a surface contour adapted to match and rest on a respective part of the bone, said resting bases are configured to be coupled to at least two of said plurality of fastening members in a second operating step, and
wherein said aligner comprises a connecting bridge connected to said resting bases, the aligner having a shape based on a new and correct inclination that the two bone parts must have with respect to one another to achieve a correct and final anatomical position, said connecting bridge defining a distance between said resting bases and a mutual inclination of the resting bases relative to one another based on the new and correct inclination that said two parts of the bone must have to achieve the correct and final anatomical position.

2. The kit according to claim 1, wherein each of said at least two positioning and fixing arms have a lower surface and at least one fastener lip, each lower surface having a contour adapted to match a surface of the bone to allow for correct and unique positioning, each at least one fastener lip adapted to grasp an edge of the bone to be cut, said at least two positioning and fixing arms extending towards said first end of said first main body.

3. The kit according to claim 1, wherein said plurality of fastening members comprises a first fastening member and a second fastening member, wherein said at least two positioning and fixing arms comprise a first arm and a second arm, wherein the first arm has a first sleeve inside which the first fastening member can be inserted and the second arm has a second sleeve inside which the second fastening member can be inserted, wherein each of said first and said second sleeves has a side opening to allow disengagement of the first main body from the first and second fastening members.

4. The kit according to claim 3, wherein the plurality of fastening members comprises a third fastening member and the cutting guide comprises a third sleeve connected to the first main body, the third sleeve adapted for insertion of the third fastening member, the third fastening member being adapted to provide a third point for connecting said first main body to the bone to be cut, wherein said third sleeve has a side opening to allow disengagement of said first main body from the third fastening member inserted in said third sleeve.

5. The kit according to claim 3, wherein the cutting guide comprises a bushing that can be connected to a respective sleeve to achieve a stable connection between said first main body and said respective fastening members.

6. The kit according to claim 1, wherein the cutting guide comprises a positioning foot projecting from said first main body, the positioning foot adapted to correctly position said first main body on said bone to be cut, wherein said positioning foot has a lower surface and at least one fastener lip, said lower surface having a contour adapted to match a surface of the bone to allow for correct and unique positioning, said at least one fastener lip adapted to grasp an edge of the bone to be cut, said positioning foot being located in proximity of said second end of said first main body.

7. The kit according to claim 1, wherein said first main body has a curvilinear shape.

8. The kit according to claim 1, wherein said second main body has a curvilinear shape.

9. The kit according to claim 1, wherein said plurality of fastening members comprises a first fastening member and a second fastening member, said second main body has a first sleeve adapted for insertion of the first fastening member, the first sleeve positioned in proximity of the first end of said second main body, wherein said first sleeve of said second main body has a side opening to allow disengagement of the second main body from the first fastening member inserted in said first sleeve of the second main body.

10. The kit according to claim 9, wherein said second main body has a second sleeve adapted for insertion of the second fastening member, the second sleeve positioned in proximity of the first end of said second main body.

11. The kit according to claim 10, wherein said first sleeve of said second main body is connected to a bushing to provide a stable connection between said second main body and the first fastening member.

12. The kit according to claim 1, comprising:
a positioning foot extending from said second main body, the positioning foot adapted to correctly position said second main body on said bone to be cut, said positioning foot being located in proximity of the intermediate section of said second main body, wherein said positioning foot has a lower surface and at least one fastener lip, said lower surface having a contour adapted to match a surface of the bone to allow for correct and unique positioning said at least one fastener lip adapted to grasp an edge of the bone.

13. The kit according to claim 1, wherein the first resting base of said aligner has a side opening to allow insertion of one of the plurality of fastening members, said first resting base being able to be coupled to a bushing for fixing with said one of the plurality of fastening members.

14. The kit according to claim 1, comprising a pair of handles suitable to be fitted over at least two of said plurality of fastening members in order to be able to maneuver the aligner connected to said at least two of the plurality of fastening members via said bushing and correctly position the two parts of the bone relative to one another.

* * * * *